United States Patent [19]
Denis et al.

[11] Patent Number: 5,227,523
[45] Date of Patent: Jul. 13, 1993

[54] PREPARATION OF ADIPIC ACID BY HYDROCARBONYLATION OF PENTENIC ACIDS

[75] Inventors: Philippe Denis, Decines; Jean-Michel Grosselin, Francheville, both of France

[73] Assignee: Rhone-Poulenc Chimie, Courbevoie, France

[21] Appl. No.: 761,497

[22] Filed: Sep. 18, 1991

[30] Foreign Application Priority Data

Sep. 28, 1990 [FR] France ............................... 9012214

[51] Int. Cl.$^5$ .............................................. C07C 51/14
[52] U.S. Cl. ............................................... 562/522
[58] Field of Search ...................................... 562/522

[56] References Cited

U.S. PATENT DOCUMENTS

| | | | |
|---|---|---|---|
| 3,989,747 | 11/1976 | Craddock et al. | 562/522 |
| 4,433,165 | 2/1984 | Singleton | 562/522 |
| 4,622,423 | 11/1986 | Burke | 562/522 |
| 4,788,334 | 11/1988 | Burke | 562/522 |
| 4,861,912 | 8/1989 | Drent et al. | 562/522 |

FOREIGN PATENT DOCUMENTS

| | | |
|---|---|---|
| 0188209 | 7/1986 | European Pat. Off. |
| 0274076 | 7/1988 | European Pat. Off. |

*Primary Examiner*—Arthur C. Prescott
*Attorney, Agent, or Firm*—Burns, Doane, Swecker & Mathis

[57] ABSTRACT

Adipic acid is selectively prepared, in good yields, by reacting at least one pentenic acid with water and carbon monoxide, the partial pressure of which, measured at 25° C., being less than or equal to 12 bar, in the presence of a catalytically effective amount of a rhodium-based catalyst and at least one iodine-containing promoter therefor, at a temperature ranging from 100° to 240° C. and at superatmospheric pressure, and in a liquid reaction medium which comprises at least one hydrocarbon or chlorocarbon solvent, whether a saturated aliphatic or cycloaliphatic hydrocarbon, aromatic hydrocarbon or chlorinated derivative thereof.

16 Claims, No Drawings

PREPARATION OF ADIPIC ACID BY HYDROCARBONYLATION OF PENTENIC ACIDS

CROSS-REFERENCE TO COMPANION APPLICATION

Our copending application Ser. No. 761,459 filed Sep. 18, 1991, now U.S. Pat. No. 5,198,577, filed concurrently herewith and assigned to the assignee hereof.

BACKGROUND OF THE INVENTION

1. Field of the Invention

The present invention relates to the preparation of adipic acid by hydrocarboxylation of pentenic acids and, more especially, to the preparation of adipic acid by reacting water and carbon monoxide with at least one pentenic acid, in the presence of a rhodium-based catalyst and of at least one iodine-containing promoter therefor.

2. Description of the Prior Art

Published European Patent Application No. 188,209 describes a process for the preparation of linear dicarboxylic acids, in particular adipic acid, by reacting unsaturated monocarboxylic acids, in particular 3-pentenoic acid, with carbon monoxide and water in the presence of a rhodium-based catalyst and an iodine-containing promoter, the reaction being conducted in a solvent such as methylene chloride at a temperature of 100° to 240° C. and under a total pressure of from 14 to 240 atm; a temperature of from 150° to 180° C. and a total pressure of from 24 to 40 atmospheres are considered to be preferable. The partial pressure of carbon monoxide typically ranges from 10 to 35 atm and preferably from 10 to 17 atm. The selection of the solvent is considered to be critical according to such '209 application.

It too is noted that nonpolar solvents such as cyclohexane and toluene are undesirable because of their propensity to promote directly the formation of branched final products and, indirectly, saturated monocarboxylic acids.

Published European Patent Application No. 0,274,076 describes a process for the preparation of linear carboxylic acids by hydroxycarboxylation of unsaturated esters or of terminally unsaturated alkenes having from 4 to 16 carbon atoms in the presence of a rhodium-based catalyst and an iodine-containing promoter therefor. The reaction is conducted in a solvent indiscriminately selected from among methylene chloride, 1,2-dichloroethane and aromatic solvents, and an aliphatic or aromatic acid having a pKa ranging from 4.2 to 5.2 is present as a reaction accelerator. The partial pressure of the carbon monoxide ranges from 10 to 200 and preferably from 13 to 20 atm.

However, when employing pentenic ester starting materials, the formation of monomethyl esters of adipic acid is characteristic thereof.

SUMMARY OF THE INVENTION

Accordingly, a major object of the present invention is the provision of an improved process for the selective production of adipic acid by hydrocarboxylation of pentenic acids in the presence of a rhodium-based catalyst and an iodine-containing promoter therefor, in a solvent selected from among the saturated aliphatic or cycloaliphatic hydrocarbons, the aromatic hydrocarbons, or chlorinated derivatives thereof.

Briefly, the present invention features a process for the preparation of adipic acid, comprising reacting water and carbon monoxide with at least one pentenic acid, in the presence of a catalytically effective amount of a rhodium-based catalyst and of at least one iodine-containing promoter therefor, at a temperature ranging from 100° to 240° C., at a pressure which is greater than atmospheric pressure, and further wherein:

(a) the reaction is carried out in at least one solvent selected from among the saturated aliphatic or cycloaliphatic hydrocarbons, the aromatic hydrocarbons, or chlorinated derivatives thereof, and (b) the partial pressure of the carbon monoxide, measured at 25° C., is less than 12 bar.

DETAILED DESCRIPTION OF THE PREFERRED EMBODIMENTS OF THE INVENTION

More particularly according to the present invention, by the term "pentenic acid" are intended 2-pentenoic acid, 3-pentenoic acid, 4-pentenoic acid and mixtures thereof.

4-Pentenoic acid provides very good results, but is only difficultly available commercially.

3-Pentenoic acid, either alone or mixed with the isomer thereof, is more particularly advantageous, in light of the general availability thereof and the satisfactory results which it provides per the process of the invention.

The process according to the present invention requires the presence of a rhodium-based catalyst. Any rhodium source is suitable for this purpose.

Exemplary rhodium sources suitable for carrying out the process of the invention include:

Rh metal; $Rh_2O_3$;
$RhCl_3$; $RhCl_3.3H_2O$;
$RhBr_3$; $RhBr_3.3H_2O$;
$RhI_3$; $Rh(NO_3)_3$; $Rh(NO_3)_3.2H_2O$;
$Rh_2(CO)_4Cl_2$; $Rh_2(CO)_4Br_2$; $Rh_2(CO)_4I_2$;
$Rh(CO)Cl[P(C_6H_5)_3]_2$;
$Rh[P(C_6H_5)_3]_2(CO)I$;
$Rh[P(C_6H_5)_3]_3Br$;
$Rh_4(CO)_{12}$; $Rh_6(CO)_{16}$; $Rh(CO)_2(acac)$;
$Rh(Cod)(acac)_2$; $Rh(acac)_3$;
$Rh_2(Cod)_2Cl_2.Rh_2(CO_2CH_3)_4$;
$HRh(CO)[P(C_6H_5)_3]_3$;

(Cod = 1,5-cyclooctadiene; acac = acetylacetonate)

The following rhodium sources are more particularly preferred for carrying out the process of the invention:
$HRh(CO)[P(C_6H_5)_3]_3$;
$Rh(CO)Cl[P(C_6H_5)_3]_2$;
$Rh_2(Cod)_2Cl_2$;
$Rh_2(CO)_4Cl_2$;
$RhI_3$; $RhCl_3.3H_2O$; $Rh(acac)_3$;
$Rh(Cod)(acac)_2$; $Rh_2(CO_2CH_3)_4$; $Rh_4(CO)_{12}$; and $Rh_6(CO)_{16}$.

The quantity of rhodium to be used may vary over wide limits.

In general, a quantity ranging from $10^{-3}$ to $10^{-1}$, expressed in moles of metallic rhodium per liter of reaction mixture, provides satisfactory results. Smaller quantities can be used; however, it is found that the reaction rate is low. The only disadvantages of larger quantities are those of economy.

The concentration of rhodium preferably ranges from $5 \times 10^{-3}$ to $10^{-2}$ (inclusive) mol/l.

By "iodine-containing promoter" according to the present invention are intended HI and organoiodine compounds capable of generating HI under the conditions of reaction and, in particular, $C_1$–$C_{10}$ alkyl iodides, with methyl iodide being more particularly preferred.

The quantity of the iodine-containing promoter to be used is typically such that the I/Rh molar ratio is greater than or equal to 0.1. It is not desirable that this ratio should exceed 20. The I/Rh molar ratio preferably ranges from 1 to 4, inclusive.

The presence of water is critical and indispensable for conducting the process according to the present invention. The quantity of water to be used is typically such that the water/pentenic acid(s) molar ratio ranges from 1 to 10, inclusive.

A smaller quantity presents the disadvantage of limiting the conversion. A larger quantity is not desirable, because of the loss in catalyst activity which is observed.

In an essential characteristic of the present invention, the reaction is carried out in at least one solvent selected from among the saturated aliphatic or cycloaliphatic hydrocarbons, the aromatic hydrocarbons, or the chlorinated derivatives thereof.

The precise nature of the solvent selected from among those indicated above is not critical according to the invention, provided that it is in the liquid state under the conditions of reaction.

Exemplary such solvents include benzene, toluene, chlorobenzene, methylene chloride, hexane and cyclohexane.

Toluene and chlorobenzene are particularly preferred for carrying out the process according to the invention.

The quantity of solvent which is present in the reaction mixture may vary over wide limits, for example from 10% to 99%, inclusive, by volume of the reaction mixture. This quantity preferably ranges from 30% to 90% by volume, inclusive.

It is another essential characteristic of the process of the invention that the partial pressure of the carbon monoxide, measured at 25° C., be less than 12 bar.

When the partial pressure of the carbon monoxide, measured at 25° C., is higher than this value, the selectivity in respect of linear diacids among the diesters (degree of linearity) considerably diminished.

A minimum partial pressure of 0.5 bar of carbon monoxide (measured at 25° C.) is particularly advantageous.

The partial pressure of carbon monoxide, measured at 25° C., is preferably less than or equal to 8 bar.

The carbon monoxide may be employed substantially pure or of technical grade, as available commercially.

As above indicated, the reaction temperature ranges from 100° to 240° C. Advantageously, the process of the present invention is carried out at a temperature ranging from 160° to 190° C.

The reaction is conducted at a pressure which is higher than atmospheric pressure and, generally, in liquid phase.

The total pressure may vary within certain limits which will depend on the operating technique adopted, on the partial pressure of carbon monoxide and on those of the constituents of the reaction mixture at the selected reaction temperature and, if appropriate, on the autogenous pressure of the pentenic acid(s) present.

The reaction mixture contains at least one hydrocarbon or chlorocarbon solvent, water, one or more rhodium sources, one or more iodine-containing promoters and, if appropriate, all or a portion of the pentenic acid(s) introduced and the reaction products.

Upon completion of the reaction or of the time allocated thereto, the adipic acid is separated off by any suitable means, for example by crystallization and/or distillation of the carboxylic acid.

In order to further illustrate the present invention and the advantages thereof, the following specific examples are given, it being understood that same are intended only as illustrative and in nowise limitative.

EXAMPLE 1

The following materials were introduced into a 125-$cm^3$ stainless steel (HASTELLOY B2) autoclave, previously purged with argon:

(i) 160 mg (0.65 mmol) of rhodium in the form of [RhCl(COD)]$_2$;
(ii) 0.7 g (5 mmol) of $CH_3I$;
(iii) 2 g (110 mmol) of water;
(iv) 2 g (50 mmol) of 3-pentenoic acid; and
(v) 50 $cm^3$ of acetic acid.

The autoclave was closed hermetically, placed in an agitating oven and connected to a supply of CO gas under pressure. 2 bar of CO were introduced cold and the mixture was heated to 190° C. over the course of 30 minutes. When this temperature had been reached, the pressure was regulated at 20 bar.

After a reaction time of 20 minutes, the absorption of CO had ceased; the autoclave was then cooled and degassed.

The reaction was analyzed by gas phase chromatography and by high performance liquid chromatography.

The quantities of product formed (molar yield relative to the 3-pentenoic acid charged) were as follows:

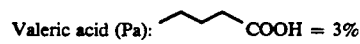

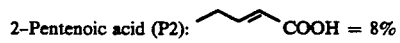

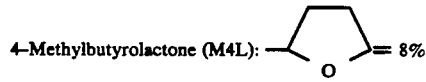

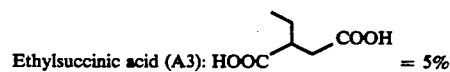

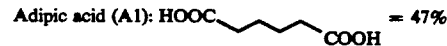

The degree of linearity (L) was 60%.
The degree of conversion of 3-pentenoic acid (TT) was 100%.

Examples 2 to 5; Control Experiments (a) to (d):

A first series of tests was carried out in the autoclave and according to the procedure described in Example 1, at 175° C. and modifying the partial pressure of the carbon monoxide and/or the nature of the solvent used.

The individual reaction conditions as well as the results obtained, all conditions being otherwise equal, are reported in Table I below, in which the conventions used are the same as in Example 1 and t represents the reaction period at temperature.

TABLE I

| Example | Solvent | P(CO) bar | t mn | TT % | Al % | L % | Pa % |
|---|---|---|---|---|---|---|---|
| 2 | Toluene | 3 | 120 | 32 | 10 | 62 | <1 |
| 3 | " | 11 | 20 | 100 | 45 | 53 | 3 |
| a | " | 18 | 20 | 100 | 36 | 43 | 3 |
| b | " | 71 | 20 | 100 | 19 | 24 | 2 |
| 4 | Chlorobenzene | 4 | 30 | 100 | 52 | 70 | 5 |
| c | Chlorobenzene | 22 | 20 | 100 | 31 | 35 | 2 |
| 5 | Methylene chloride | 8 | 20 | 100 | 55 | 61 | 2 |
| d | Methylene chloride | 25 | 20 | 100 | 38 | 44 | 1 |

These results evidence the determining effect of a low partial pressure of CO on the degree of linearity (L).

EXAMPLE 6

The procedure of Example 5 was repeated, in the autoclave and according to the procedure described above, except that the charge contained 50 mmol of 4-pentenoic acid instead of 3-pentenoic acid.

After reaction for 30 min, all conditions being otherwise equal, the results obtained were as follows:
(a) TT=100%
(b) Al=69%
(c) L=85 %
(d) Pa=1%

EXAMPLE 7

The procedure of Example 5 was repeated, in the autoclave and according to the procedure described above, except that the charge contained 50 mmol of 2-pentenoic acid instead of 3-pentenoic acid.

After reaction for 16 h, all conditions being otherwise equal, the results obtained were as follows:
(a) TT=62%
(b) Al=36%
(c) L=60%
(d) Pa=26%

EXAMPLE 8

The procedure of Example 4 was repeated, in the autoclave and according to the procedure described above, except that the temperature (150° C.) was modified.

After reaction for 60 min, the results obtained were as follows:
(a) TT=100%
(b) Al=42%
(c) L46%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the selective preparation of adipic acid, comprising reacting at least one pentenic acid with water and carbon monoxide, the partial pressure of which, measured at 25° C., being less than 12 bar, in the presence of a catalytically effective amount of a rhodium-based catalyst and at least one iodine-containing promoter therefor, at a temperature ranging from 100° to 240° C. and at superatmospheric pressure, and in a liquid reaction medium which comprises at least one hydrocarbon or chlorocarbon solvent.

2. The process as defined by claim 1, said at least one reaction solvent comprising a saturated aliphatic or cycloaliphatic hydrocarbon.

3. The process as defined by claim 1, said at least one reaction solvent comprising an aromatic hydrocarbon.

4. The process as defined by claim 1, said at least one reaction solvent comprising a chlorinated saturated aliphatic or cycloaliphatic hydrocarbon.

5. The process as defined by claim 1, said at least one reaction solvent comprising a chlorinated aromatic hydrocarbon.

6. The process as defined by claim 1, said at least one reaction solvent comprising toluene or cyclohexane.

7. The process as defined by claim 1, said at least one reaction solvent comprising at least 10% by volume of said liquid reaction medium.

8. The process as defined by claim 7, said at least one reaction solvent comprising from 30% to 90% by volume of said liquid reaction medium.

9. The process as defined by claim 1, the concentration of rhodium values in said liquid reaction medium ranging from $10^{-3}$ to $10^{-1}$ mol/l.

10. The process as defined by claim 1, wherein the I/Rh ratio in said liquid reaction medium is at least 0.1.

11. The process as defined by claim 6, said I/Rh molar ratio being no greater than 20.

12. The process as defined by claim 1, wherein the water/pentenic acid(s) molar ratio in said liquid reaction medium ranges from 1 to 10.

13. The process as defined by claim 1, carried out at a temperature ranging from 160° to 190° C.

14. The process as defined by claim 1, the partial pressure of said carbon monoxide, measured at 25° C., being less than or equal to 8 bar.

15. The process as defined by claim 1, said at least one reaction solvent comprising chlorobenzene.

16. The process as defined by claim 15, said I/Rh molar ratio being no greater than 20.

* * * * *